US012350176B2

(12) United States Patent
Woo et al.

(10) Patent No.: US 12,350,176 B2
(45) Date of Patent: Jul. 8, 2025

(54) ROBOTIC PROSTHETIC LEG AND METHOD FOR DRIVING ROBOTIC PROSTHETIC LEG

(71) Applicant: KOREA INSTITUTE OF MACHINERY & MATERIALS, Daejeon (KR)

(72) Inventors: Hyunsoo Woo, Daegu (KR); Hyukjin Lee, Gyeongsan-si (KR); Jangho Cho, Daegu (KR); Kiyoung Kim, Daegu (KR)

(73) Assignee: KOREA INSTITUTE OF MACHINERY & MATERIALS, Daejeon (KR)

( * ) Notice: Subject to any disclaimer, the term of this patent is extended or adjusted under 35 U.S.C. 154(b) by 377 days.

(21) Appl. No.: 17/429,074

(22) PCT Filed: Jan. 29, 2020

(86) PCT No.: PCT/KR2020/001326
§ 371 (c)(1),
(2) Date: Aug. 6, 2021

(87) PCT Pub. No.: WO2020/162671
PCT Pub. Date: Aug. 13, 2020

(65) Prior Publication Data
US 2022/0142793 A1 May 12, 2022

(30) Foreign Application Priority Data
Feb. 7, 2019 (KR) .................. 10-2019-0014605

(51) Int. Cl.
*A61F 2/66* (2006.01)
*A61F 2/50* (2006.01)
*A61F 2/70* (2006.01)

(52) U.S. Cl.
CPC ...... *A61F 2/6607* (2013.01); *A61F 2002/503* (2013.01); *A61F 2002/5073* (2013.01); *A61F 2002/701* (2013.01); *A61F 2002/704* (2013.01)

(58) Field of Classification Search
CPC .................. A61F 2/6607; A61F 2/66; A61F 2002/6614–6692;
(Continued)

(56) References Cited

U.S. PATENT DOCUMENTS 2,529,968 A * 11/1950 Sartin .................. A61F 2/66
623/42
3,754,286 A * 8/1973 Ryan .................... A61F 2/66
623/56
(Continued)

FOREIGN PATENT DOCUMENTS

JP          H5-239996 A       9/1993
KR   10-2005-0058417 A       6/2005
(Continued)

OTHER PUBLICATIONS

International Search Report issued May 12, 2020, corresponding to International Application No. PCT/KR2020/001326.

*Primary Examiner* — Leslie A Lopez
(74) *Attorney, Agent, or Firm* — Hauptman Ham, LLP

(57) ABSTRACT

In a robotic prosthetic leg and a method for driving the robotic prosthetic leg, the robotic prosthetic leg includes an ankle bracket, a driving part, a guide bracket, a wire, a pressing part and a first elastic member. The ankle bracket is disposed at a rear upper side of a treading member. The driving part is rotatably combined with the ankle bracket. The guide bracket has a base block and a guide conduit. The wire has a rear side connected to the driving part and extending toward a front side of the treading member. The pressing part is combined with a front side of the wire. The first elastic member is disposed between the base block and (Continued)

the pressing part to enclose the guide conduit and is configured to support the pressing part.

10 Claims, 5 Drawing Sheets

(58) Field of Classification Search
  CPC ........ A61F 2002/5072–5073; A61F 2002/701; A61F 2002/704
  See application file for complete search history.

(56) References Cited

U.S. PATENT DOCUMENTS

| | | | |
|---|---|---|---|
| 5,545,234 A * | 8/1996 | Collier, Jr. | ................ A61F 2/60 623/49 |
| 2006/0069449 A1* | 3/2006 | Bisbee, III | ................ A61F 2/64 623/46 |
| 2013/0006386 A1 | 1/2013 | Hansen et al. | |
| 2014/0088729 A1 | 3/2014 | Herr et al. | |
| 2014/0121782 A1 | 5/2014 | Herr et al. | |
| 2015/0088729 A1* | 3/2015 | Langere | ............. G06Q 30/0645 705/39 |
| 2015/0265425 A1* | 9/2015 | Aagaah | ..................... A61F 2/80 623/47 |
| 2016/0158032 A1 | 6/2016 | Ward et al. | |
| 2017/0165088 A1 | 6/2017 | Lefeber et al. | |
| 2018/0085237 A1 | 3/2018 | Gao et al. | |
| 2018/0116826 A1* | 5/2018 | Byars | ..................... A61F 2/6607 |

FOREIGN PATENT DOCUMENTS

| | | | | |
|---|---|---|---|---|
| KR | 10-1793141 | B1 | 11/2017 | |
| KR | 101994242 | B1 * | 6/2019 | ............... A61F 2/68 |

* cited by examiner

ROBOTIC PROSTHETIC LEG AND METHOD FOR DRIVING ROBOTIC PROSTHETIC LEG

CROSS-REFERENCE TO RELATED APPLICATION

This present application is a national stage filing under 35 U.S.C § 371 of PCT application number PCT/KR2020/001326 filed on Jan. 29, 2020, which is based upon and claims the benefit of priority to Korean Patent Application No. 10-2019-0014605 filed Feb. 7, 2019 in the Korean Intellectual Property Office. The disclosures of the above-listed applications are hereby incorporated by reference herein in their entireties.

BACKGROUND

1. Field of Disclosure

The present disclosure of invention relates to a robotic prosthetic leg and a method for driving the robotic prosthetic leg, and more specifically the present invention relates to a robotic prosthetic leg driven more stably and a method for driving the robotic prosthetic leg.

2. Description of Related Technology

A robot taking on risky work on behalf of people, and a prosthetic device replacing human limbs are used more widely, and thus a proper torque should be generated and the device should be designed to have a proper weight, as a function of a basic joint device capable of supporting a weight or a load and maintaining a balance.

Early commercial prosthetics were developed to replace amputated body parts from an aesthetic point of view, but recently, the prosthetics playing an important role from a functional point of view have been developed to enable natural walking and to suppress excessive metabolic consumption.

However, a sufficient torque to obtain gait momentum is generated for the natural walking, but to generate a relatively high torque with a relatively light weight is not easy in the conventional prosthetic leg.

Thus, the prosthetic leg having a relatively light weight and generating sufficient torque for the natural walking should be developed.

Related prior art is Korean laid-open patent No. 10-2005-0058417.

SUMMARY

The present invention is developed to solve the above-mentioned problems of the related arts. The present invention provides a robotic prosthetic leg capable of being driven more stably and a method for driving the robotic prosthetic leg.

The technical purposes of the present invention may not limited thereto, and various changes and modifications may be made by one ordinary skilled in the art within the spirit and scope of the present invention.

According to an example embodiment, the robotic prosthetic leg includes an ankle bracket, a driving part, a guide bracket, a wire, a pressing part and a first elastic member. The ankle bracket is disposed at a rear upper side of a treading member. The driving part is rotatably combined with the ankle bracket, to transmit a torque for the treading member to be rotated. The guide bracket has a base block and a guide conduit. The base block is disposed at the rear upper side of the treading member and is disposed at a lower side of the driving part. The guide conduit is connected to the base block and extends along a longitudinal direction of the treading member. The wire has a rear side connected to the driving part and extends toward a front side of the treading member with enclosing a lower side of the driving part. The pressing part is combined with a front side of the wire. The first elastic member is disposed between the base block and the pressing part to enclose the guide conduit, and is configured to support the pressing part toward the front side of the treading member.

In an example, the wire may extend through the guide conduit. The first elastic member may enclose the wire extending through the guide conduit. The pressing part may move a rear side of the treading member to press the first elastic member, in conjunction with a movement of wire pulling toward the rear side of the treading member, when the driving part rotates toward a front direction of the treading member.

In an example, the guide conduit may have a first outer diameter smaller than an inner diameter of the first elastic member. The fixing part may be formed at a rear side of the guide conduit and the fixing part may have a second outer diameter corresponding to the inner diameter of the first elastic member.

In an example, the robotic prosthetic leg may further include a support bracket and an adjusting part. The support bracket may be disposed at a upper side of the driving part, and have an adjusting opening through which a rear side of the wire passes. The adjusting part may have a stopper and an adjuster. The stopper may be combined with the rear side of the wire which passes through the adjusting opening to be extended to an outside of the adjusting opening. The adjuster may be screwed together with the adjusting opening and may be closely rotated with respect to the stopper to adjust a height of the stopper.

In an example, the robotic prosthetic leg may further include a second elastic member disposed between the ankle bracket and the driving part. The second elastic member may provide an elastic force so as to maintain an angle between the driving part and the treading member to be a predetermined basic angle, when an external force is not applied.

In an example, the second elastic member may be a torsion spring. The driving part may have a first fixing hole at which a first end of the second elastic member is inserted and fixed. The ankle bracket may have a second fixing hole at which a second end of the second elastic member is inserted and fixed.

In an example, the ankle bracket may further include a fixing protrusion with which the second elastic member is rolled up, and an incision hole through which the first end of the second elastic member passes, so that the first end of the second elastic member extends to outside.

According to another example embodiment, the method for driving the prosthetic leg includes a treading step, a rolling step and a toe-off step. In the treading step, the treading member treads a ground and the driving part rotates toward a front direction of the treading member, so that the wire is pulled backwardly and the first elastic member is compressed by the pressing part. In the rolling step, the driving part rotates toward a rear direction of the treading member, so that the treading member kicks the ground. In the toe-offing step, the treading member is off the ground.

In an example, in the rolling step, the first elastic member may be elongated to provide an additional rotating force so that the driving part may rotate toward a rear direction of the treading member.

In an example, a second elastic member may be disposed between the ankle bracket and the driving part. A first end of the second elastic member may be fixed to the driving part and a second end of the second elastic member may be fixed to the ankle bracket. The second elastic member may provide an elastic force so as to maintain an angle between the driving part and the treading member to be a predetermined basic angle, in the toe-offing step.

According to the present example embodiments, a rolling movement in which the treading member kicks the ground may be performed due to the rotational force provided by the driving part, and the additional rotational force due to an elastic restoring force which is generated as the first elastic member having the compressed energy is elongated. Thus, the load of the driving part may be decreased.

In addition, as the treading member is off the ground to be a toe-offing state, the treading member is maintained to have a uniform angle with the driving part due to the restoring force of the second elastic member. Thus, the treading member is prevented from being pulled and touched by the ground in cases that the driving part is not operated.

The effects of the present invention may not limited thereto, and the effects from various changes and modifications of the present invention made by one ordinary skilled in the art within the spirit and scope of the present invention may be also included.

Figure 1:
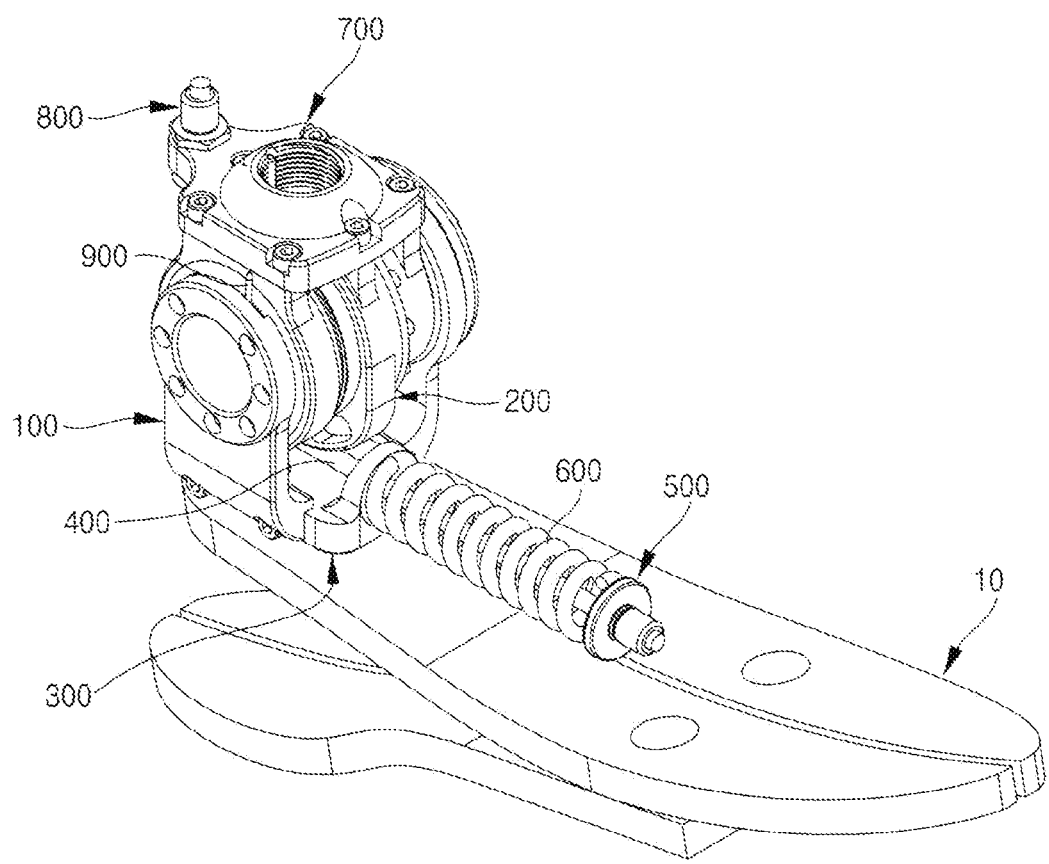
FIG. 1 is a perspective view illustrating a robotic prosthetic leg according to an example embodiment of the present invention.

| * reference numerals | |
|---|---|
| 10: treading member | 100: ankle bracket |
| 110: first ankle bracket | 200: driving part |
| 300: guide bracket | 330: guide conduit |
| 400: wire | 500: pressing part |
| 600: first elastic member | 700: support bracket |
| 800: adjusting part | 900: second elastic member |

DETAILED DESCRIPTION

The invention is described more fully hereinafter with Reference to the accompanying drawings, in which embodiments of the invention are shown. Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

It will be understood that, although the terms first, second, third etc. may be used herein to describe various elements, components, regions, layers and/or sections, these elements, components, regions, layers and/or sections should not be limited by these terms. These terms are only used to distinguish one element, component, region, layer or section from another region, layer or section. Thus, a first element, component, region, layer or section discussed below could be termed a second element, component, region, layer or section without departing from the teachings of the present invention. Spatially relative terms, such as "beneath," "below," "lower," "above," "upper" and the like, may be used herein for ease of description to describe one element or feature's relationship to another element(s) or feature(s) as illustrated in the figures.

The terminology used herein is for the purpose of describing particular embodiments only and is not intended to be limiting of the invention. As used herein, the singular forms "a," "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The invention is described more fully hereinafter with reference to the accompanying drawings, in which embodiments of the invention are shown.

Figure 2:
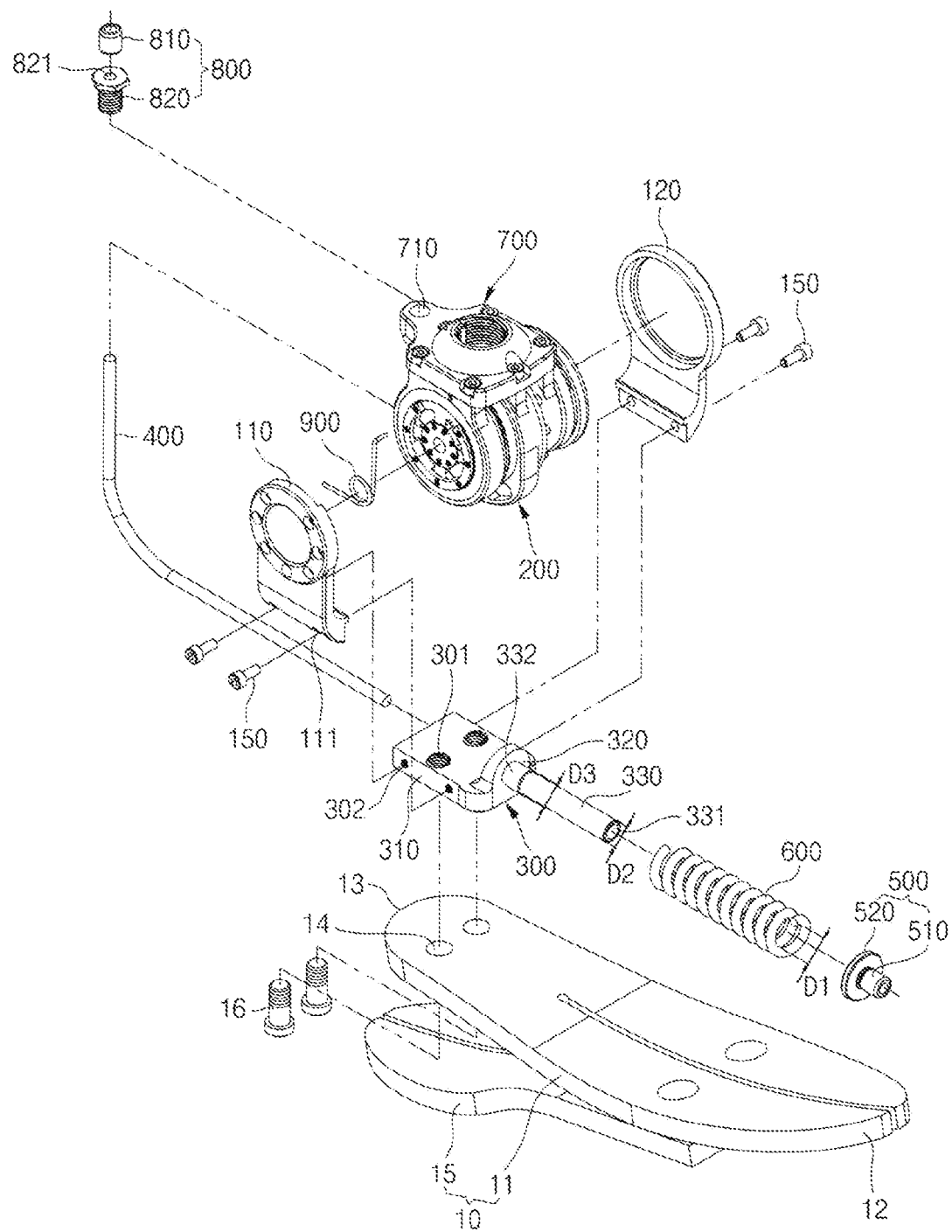
FIG. 2 is an exploded perspective view illustrating the robotic prosthetic leg of FIG. 1.

FIG. 1 is a perspective view illustrating a robotic prosthetic leg according to an example embodiment of the present invention. FIG. 2 is an exploded perspective view illustrating the robotic prosthetic leg of FIG. 1.

Referring to FIG. 1 and FIG. 2, the robotic prosthetic leg includes a driving part 200, a guide bracket 300, a pressing part 500 and a first elastic member 600.

A treading member 10 corresponds to a human foot. For example, the treading member 10 includes a sole part 11 and a heel part 15, but not limited thereto.

Hereinafter, for the convenience of the explanation, with respect to an extending direction of the treading member 10, a front side/a front portion/a front direction or a rear side/a rear portion/a rear direction may be used. That is, a front portion 12 of the treading member 10 may be explained as the front side, the front portion or the front direction, and a rear portion 13 of the treading member 10 may be explained as the rear side, the rear portion or the rear direction.

The ankle bracket 100 is disposed at an upper side of the rear side 13 (rear upper side) of the treading member 10.

The ankle bracket 100 includes a first ankle bracket 110 and a second ankle bracket 120 spaced apart from each other.

The driving part 200 is combined with the ankle bracket 100 and is rotated with respect to the ankle bracket 100. For example, the driving part 200 may be combined between the first ankle bracket 110 and the second ankle bracket 120.

The driving part 200 generates a rotating torque, and is rotated toward the front direction 12 of the treading member 10 (clockwise direction in the figures) or toward the rear direction 13 of the treading member 10 (counterclockwise direction in the figures) with respect to the ankle bracket 100. Thus, when the driving part 200 is fixed, the ankle bracket 100 may be rotated in both directions due to the rotating torque of the driving part 200. Thus, in the treading member 10 combined with the ankle bracket 100, the front side 12 of the treading member 10 may be upwardly or downwardly driven. Accordingly, the ankle bracket 100 and the driving part 200 may function as a human ankle.

The guide bracket 300 is disposed at an upper side of the rear side 13 (rear upper side) of the treading member 10, and includes a base block 310 and a guide conduit 330.

The base block 310 is disposed between the first ankle bracket 110 and the second ankle bracket 120, and the base block 310 is disposed at a lower side of the driving part 200.

A first combining hole 301 is formed at the base block 310. The first combining hole 301 passes through the base block 310 along a vertical direction, and a plurality of first combining holes may be formed.

A first through hole 14 is formed through the sole part 11 of the treading member 10 and the first through hole 14 is aligned with the first combining hole 301. A first combining member 16 is combined through the first through hole 14 and the first combining hole 301. Thus, the base block 310 may be tightly combined with the sole part 11.

A second combining hole 302 is formed at the base block 310. The second combining hole 302 passes through the base block 310 along a horizontal direction, and a plurality of second combining holes may be formed.

A second through hole 111 is formed through the first and second ankle brackets 110 and 120, and the second through hole 111 is aligned with the second combining hole 302. A second combining member 150 is combined through the second through hole 111 and the second combining hole 302. Thus, the first and second ankle brackets 110 and 120 may be tightly combined with the base block 310.

A support block 320 is formed at an upper front side of the base block 310. The support block 320 is protruded upwardly, and the support block 320 has a diameter larger than an outer diameter of the first elastic member 600 explained below. Thus, a rear side of the first elastic member 600 may be stably fixed by the support block 320.

The guide conduit 330 is connected to the base block 310, and the guide conduit 330 extends along a longitudinal direction of the treading member 10. For example, a rear side of the guide conduit 330 may be connected to the support block 320, and the guide conduit 330 may extend toward the front direction 12 of the treading member 10. A guide hole 331 passes through the guide conduit 330 along a central axis, and the guide hole 331 passes through the guide conduit 330 to reach the support block 320. That is, the guide hole 331 is formed to pass through the guide conduit 330 from a front side of the guide conduit 330 to a rear side of the support block 320.

A rear side of the wire 400 is connected to a rear side of the driving part 200, and the wire 400 encloses a lower side of the driving part 200 to be extended toward the front direction 12 of the treading member 10. The wire 400 passes through the guide hole 331. A diameter of the wire 400 is smaller than an inner diameter of the guide hole 331, and thus the wire 400 may move forwardly and backwardly in the guide conduit 330 along the longitudinal direction of the guide conduit 330, with inserted into the guide hole 331. The wire 400 has a uniform length, and thus the wire 400 may include a material without flexibility or elasticity. Thus, the wire 400 may be less or may not be elongated or contracted.

The pressing part 500 is combined at a front side of the wire 400. The pressing part 500 includes a fasten part 510 and a pressing plate 520.

The fasten part 510 fastens a front side of the wire 400 to prevent the wire 400 from being separated.

The pressing plate 520 is connected to a rear side of the fasten part 510. The pressing plate 520 has a diameter larger than an outer diameter of the first elastic member 600. Thus, a front side of the first elastic member 600 may be stably fixed by the pressing plate 520.

The first elastic member 600 is disposed between the base block 310 and the pressing part 500. The first elastic member 600 encloses the guide conduit 330. In addition, the first elastic member 600 may further enclose the wire 400 exposed to outside through the front side of the guide conduit 330.

A rear side of the first elastic member 600 is tightly attached to the support block 320, and a front side of the first elastic member 600 is tightly attached to the pressing plate 520.

The first elastic member 600 may be a coil spring, and may be a compression spring storing a compressed force. Since the base block 310 is fixed at the sole part 11, the first elastic member 600 generates a restoring force toward the front direction 12 of the treading member with respect to the support block 320. Thus, the first elastic member 600 elastically supports the pressing part 500 along the front direction 12 of the treading member 10.

The robotic prosthetic leg may further include a support bracket 700 and an adjusting part 800.

The support bracket 700 is disposed at an upper side of the driving part 200. The support bracket 700 is connected to a user's leg. The support bracket 700 includes an adjusting opening 710. The adjusting opening 710 is formed at a rear side of the support bracket 700, and a rear side of the wire 400 passes through the adjusting opening 710 to extend upwardly.

The adjusting part 800 includes a stopper 810 and an adjuster 820.

The stopper 810 is combined with a rear side of the wire 400 passing through the adjusting opening 710, and the stopper 810 fastens the rear side of the wire 400 to prevent the wire 400 from being separated.

The adjuster 820 is screwed together with the adjusting opening 710, and has a third through hole 821 formed through the adjuster 820 along an axis direction. The third through hole 821 has an inner diameter larger than the diameter of the wire 400, and thus, the wire 400 moves upwardly and downwardly with inserted into the third through hole 821.

The adjuster 820 is tightly attached to a lower side of the stopper 810. Thus, as the adjuster 820 rotates with combined with the adjusting opening 710, a height of the stopper 810 may be adjusted. Here, as the height of the stopper 810 increases, the wire 400 is pulled toward the rear side, and as the height of the stopper 810 decreases, the wire 400 is released toward the front side. As the wire 400 is pulled toward the rear side, the first elastic member 600 is compressed more due to the pressing part 500 and thus the elastic restoring force at an initial state is increased. In contrast, as the wire 400 is released toward the front side, the first elastic member 600 is compressed less due to the pressing part 500 and thus the elastic restoring force at the initial state is decreased. Accordingly, a height of a hoof of the user wearing the robotic prosthetic leg, a length of the hoof of the user and so on may be properly adjusted.

The guide conduit 330 has a first outer diameter D2 smaller than an inner diameter D1 of the first elastic member 600.

Thus, as the first elastic member 600 is compressed by the pressing part 500 which moves backwardly in conjunction with the movement of the wire 400 pulling toward the rear side of the treading member 10, the first elastic member 600 is stably compressed even though a shape of the compressed first elastic member 600 becomes unevenly bumpy.

In addition, a fixing end 332 is formed at the rear side of the guide conduit 330, and the fixing end 332 has a second outer diameter D3 corresponding to the inner diameter D1 of the first elastic member 600.

Thus, the rear side of the first elastic member 600 is inserted and combined with the fixing end 332, and thus the first elastic member 600 is tightly combined with the guide conduit 330.

The robotic prosthetic leg may further include a second elastic member 900.

The second elastic member 900 is disposed between the ankle bracket 100 and the driving part 200, and here, the second elastic member 900 may be disposed between the first ankle bracket 110 and the driving part 200.

The second elastic member 900 provides an elastic force to maintain an angle between the driving part 200 and the treading member 10 to be a predetermined basic angle, when an external force is not applied.

Figure 3A:
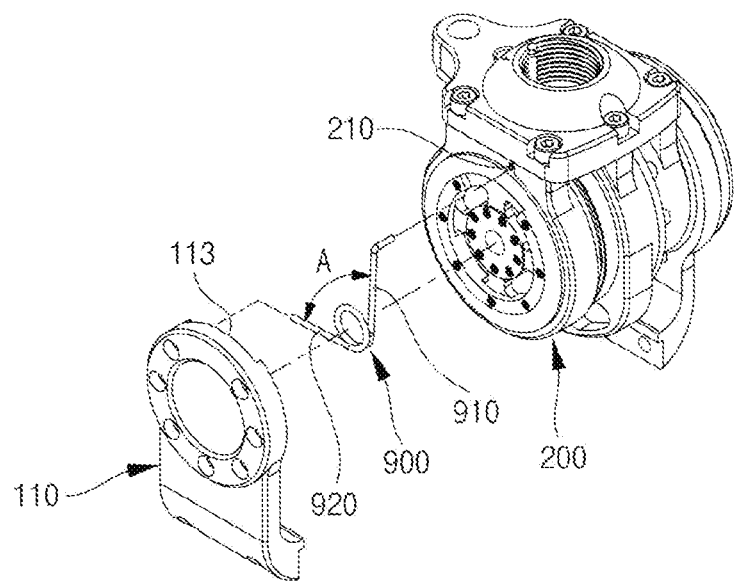
FIG. 3A and FIG. 3B are exploded perspective views illustrating a second elastic member of the robotic prosthetic leg of FIG. 1.
Figure 3B:
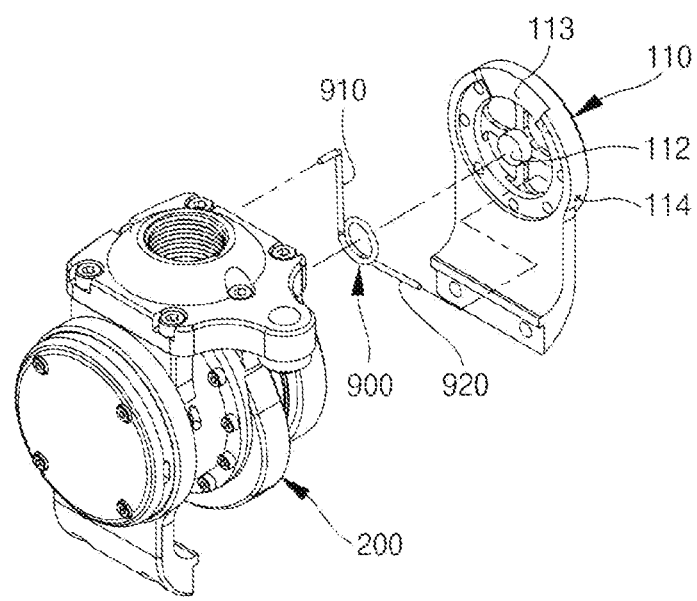

FIG. 3A and FIG. 3B are exploded perspective views illustrating a second elastic member of the robotic prosthetic leg of FIG. 1.

Referring to FIG. 3A and FIG. 3B, the second elastic member 900 may be a torsion spring.

The driving part 200 has a first fixing hole 210. The first fixing hole 210 is formed along a rotational axis direction of the driving part 200. A first end of the second elastic member 900 is curved to be inserted and fixed to the first fixing hole 210.

In addition, the first ankle bracket 110 has a second fixing hole 114. The second fixing hole 114 is formed along a circumferential direction of the first ankle bracket 110. A second end of the second elastic member 900 is inserted and fixed to the second fixing hole 114.

Accordingly, as the driving part 200 rotates, the first end 910 of the second elastic member 900 rotates together with the driving part 200, and thus an angle between the first end 910 of the second elastic member 900 and the second end 920 of the second elastic member 900 is changed to generate the elastic restoring force at the second elastic member 900.

Here, as illustrated in the figure, at the initial state before the driving, the first fixing hole 210 is disposed at an upper side of the rotational axis of the driving part 200, and the second fixing hole 114 is disposed at a side along the circumferential direction of the first ankle bracket 110. Thus, an angle between the first fixing hole 210 and the second fixing hole 114 may be perpendicular, and thus both ends of the second elastic member 900 may extend perpendicular to each other.

However, although not shown in the figure, the positions of the first and second fixing holes 210 and 114 may be variously changed with both ends of the second elastic member 900 being inserted to the first and second fixing holes 210 and 114, considering the position or the angle of both ends of the second elastic member 900.

Further, the shape of the second elastic member 900 as illustrated in the figure, is formed at the initial state before the driving of the driving part 200, and thus the angle formed by both ends of the second elastic member 900 may be changed according to the driving of the driving part 200.

The first end 910 and the second end 920 of the second elastic member 900 may form a predetermined basic angle A. Thus, as the angle between the ankle bracket 100 and the driving part 200 is changed due to the rotation of the driving part 200 with respect to the ankle bracket 100, the angle between the first and second ends 910 and 920 of the second elastic member 900, and then the elastic restoring force is generated at the second elastic member 900 since the second elastic member 900 is forced to be restored to the predetermined basic angle A.

Further, the first ankle bracket 110 may further include a fixing protrusion 112 and an incision hole 113.

The second elastic member 900 is rolled up with the fixing protrusion 112. The fixing protrusion 112 is formed at a rotational center of the driving part 200, and thus a center of the second elastic member 900 is positioned at the rotational center of the driving part 200.

The first end 910 of the second elastic member 900 passes through the incision hole 113, and then the first end 910 thereof extends to outside.

The incision hole 113 has a uniform length along a circumferential direction, and thus when the driving part 200 rotates, the first end 910 of the second elastic member 900 stably rotates together with the driving part 200 with the first end of the second elastic member 900 combined with the first fixing hole 210.

Figure 4A:
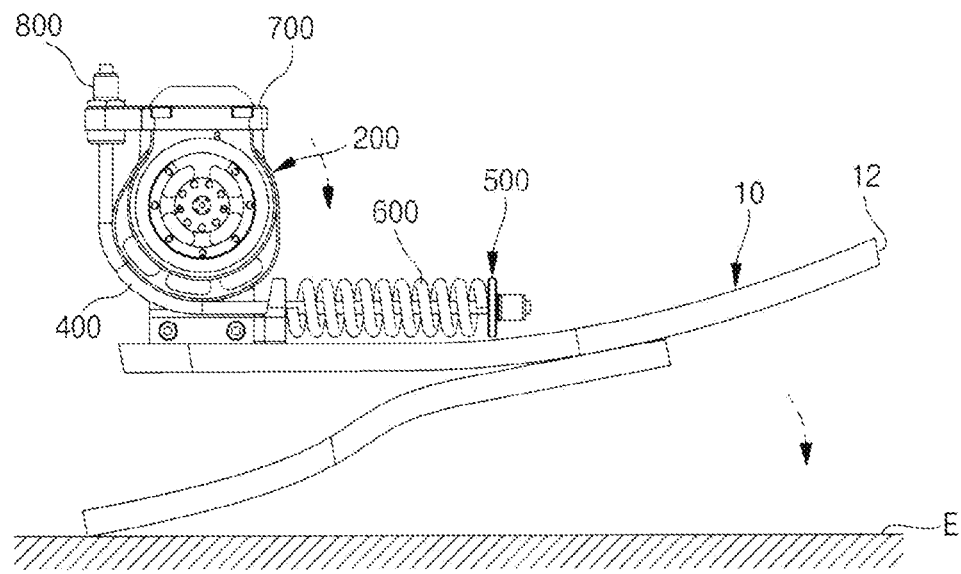
FIG. 4A and FIG. 4B are operating views of the robotic prosthetic leg of FIG. 1.
Figure 4B:
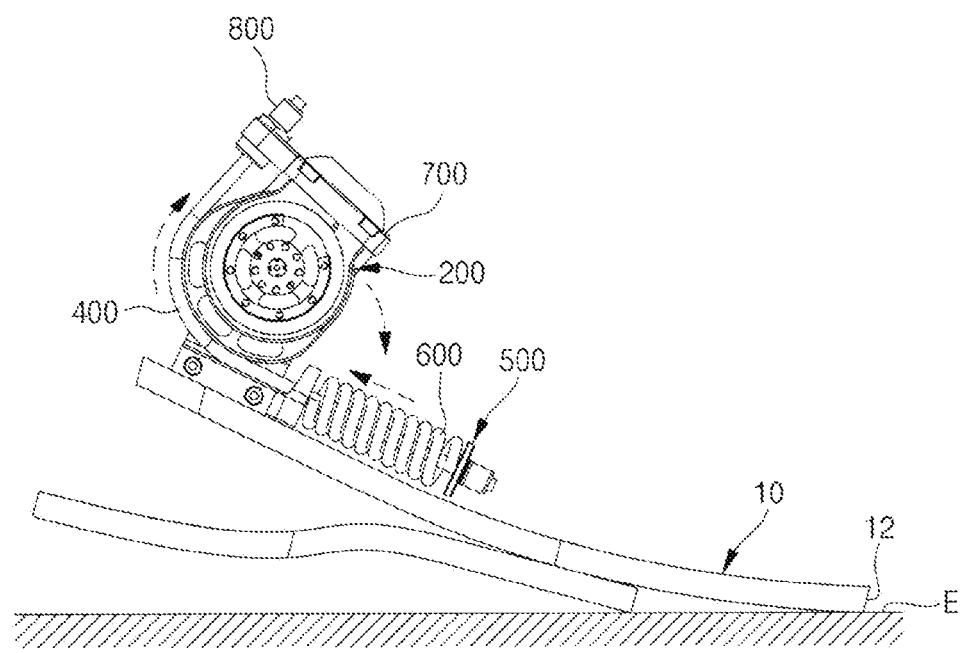

FIG. 4A and FIG. 4B are operating views of the robotic prosthetic leg of FIG. 1. FIG. 4A shows a state before the treading member 10 touches a ground E, and FIG. 4B shows a state when the treading member 10 touches the ground E. Hereinafter, FIG. 1 to FIG. 3B are also referred in addition to FIG. 4A and FIG. 4B.

Referring to FIG. 4A, at a toe-offing state in which the treading member 10 is off the ground E, the driving part 200 generates a power to maintain the angle between the driving part 200 and the ankle bracket 100 uniformly. Thus, the front side 12 of the treading member 10 is prevented from being sagged. However, when an electricity is not supplied to the driving part 200 or the driving part 200 dose not generate the power due to malfunction or other reasons, the power to maintain the above angle uniformly is not supplied and thus the front side 12 of the treading member 10 rotates downwardly due to a self-weight of the treading member 10.

However, in the present example embodiment, the second elastic member 900 is configured, to provide the elastic force to maintain the angle between the driving part 200 and the treading member 10 to be the predetermined basic angle at the toe-offing state. Thus, even though the driving part 200 is not operated normally, the front side 12 of the treading member 10 is prevented from being sagged.

In the state of the toe-offing and in the state that the power for maintaining the angle between the driving part 200 and the ankle bracket 100 is not supplied, the angle between the driving part 200 and the treading member 10 formed by the second elastic member 900 may be adjusted according as the basic angle A of the second elastic 900 is formed. As in the present example, when the second elastic member 900 forms the basic angle A to be 90°, the angle between the driving part 200 and the treading member 10 may be maintained to be 90°, even though the power is not supplied and in the toe-offing state.

Then, as illustrated in FIG. 4b, as the treading member 10 treads the ground E and then the driving part 200 rotates toward the front direction 12 (clockwise direction) of the treading member 10 to decrease the angle between the driving part 200 and the treading member 10 less than 90°, the wire 400 is pulled toward the rear upper side. Then, as the result of the conjunction, the pressing part 500 presses the first elastic member 600 and the first elastic member 600 is compressed.

Then, as the driving part 200 rotates toward the rear direction (counterclockwise direction) of the treading member 10, which means that the front side 12 of the treading member 10 rotates downwardly and then the treading member 10 performs a rolling operation at which the treading member 10 kicks the ground E, the wire is pushed out forwardly. Then, the compressed first elastic member 600 is released or elongated to supply the additional rotating force so that the driving part 200 rotates toward the rear direction (counterclockwise direction) of the treading member 10. That is, the additional rotating force is supplied so that the front side 12 of the treading member 10 rotates downwardly with respect to the driving part 200 and then the treading member 10 kicks the ground E. Accordingly, due to the rotating force supplied by the driving part 200 and the additional rotating force due to the elastic restoring force generated by the elongation of the first elastic member 600 having the compressed energy, the treading member 10 kicks the ground E which is the rolling operation. Here, the addition rotating force due to the first elastic member 600 may decrease the load of the driving part 200.

In addition, when the driving part 200 rotates toward the front side (clockwise direction) of the treading member 10, the first end 910 of the second elastic member 900 rotates together with the driving part 200 and thus the angle between the first and second ends of the second elastic member 900 is increased over the predetermined basic angle.

Thus, the restoring force to restore the increased angle to be the basic angle is generated, and the restoring force is applied for the front side 12 of the treading member 10 to rotate downwardly when the angle of the driving part 200 is fixed. Thus, the rotating force provided by the second elastic member 900 may reduce the load of the driving part 200 more, when the treading member 10 kicks the ground E at the rolling operation.

When the rolling operation is finished and the treading member 10 is off the ground E and thus in the toe-offing state, the treading member 10 is maintained to have a uniform angle with the driving part 200 due to the restoring force of the second elastic member 900.

Hereinafter, a method for driving the robotic prosthetic leg is explained.

Figure 5:
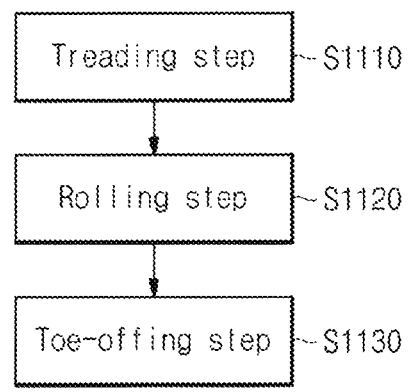
FIG. 5 is a flow chart showing a method for driving the robotic prosthetic leg of FIG. 1.

FIG. 5 is a flow chart showing a method for driving the robotic prosthetic leg of FIG. 1.

Referring to FIG. 5, the method for driving the robotic prosthetic leg includes a treading step S1110, a rolling step S1120 and a toe-offing step S1130.

In the treading step S1110, the treading member treads the ground, the driving part rotates toward the front side of the treading member, and then the wire is pulled backwardly. Thus, the first elastic member is compressed by the pressing part.

In the rolling step S1120, the driving part rotates toward the rear side of the treading member and then the treading member kicks the ground.

In the rolling step S1120, when the treading member is off the ground, the compressed first elastic member is elongated to supply the additional rotating force which forces to rotate the driving part to the rear side of the treading member.

In addition, in the rolling step S1120, the second elastic member may supply the force additionally so as for the treading member to kick the ground.

In the toe-offing step S1130, the treading member is off the ground.

In the toe-offing step S1130, the second elastic member supplies the elastic force to maintain the angle between the driving part and the treading member to be the predetermined basic angle. Thus, the treading member is prevented from being touched or pulled on the ground, even though the driving part is not operated.

This invention may, however, be embodied in many different forms and should not be construed as limited to the embodiments set forth above. Rather, these embodiments are provided so that this disclosure will be thorough and complete, and will fully convey the scope of the invention to those skilled in the art. In the drawings, the size and relative sizes of layers and regions may be exaggerated for clarity.

Although the exemplary embodiments of the present invention have been described, it is understood that the present invention should not be limited to these exemplary embodiments but various changes and modifications can be made by one ordinary skilled in the art within the spirit and scope of the present invention as hereinafter claimed.

What is claimed is:

1. A robotic prosthetic leg comprising:
   an ankle bracket having first and second ankle brackets spaced apart from each other, wherein the first and second ankle brackets are connected with a rear upper side of a treading member;
   a driving part rotatably combined with the first and second ankle brackets and disposed between the first and second ankle brackets, and configured to transmit torque for the treading member to be rotated;
   a guide bracket having a base block and a guide conduit, wherein the base block is disposed between the rear upper side of the treading member and a lower side of the driving part, wherein the guide conduit is connected to the base block and extends along a longitudinal direction of the treading member;
   a wire having a rear end connected to the driving part and extending toward a front side of the treading member;
   a pressing part combined with a front end of the wire; and
   a first elastic member disposed between the base block and the pressing part to enclose the guide conduit, and configured to support the pressing part toward the front side of the treading member,
   wherein the wire passes through the guide conduit and is combined with the pressing part, and
   wherein the first elastic member encloses the guide conduit through which the wire passes.

2. The robotic prosthetic leg of claim 1,
   wherein the pressing part moves a rear side of the treading member to press the first elastic member, in conjunction with a movement of wire pulling toward the rear side of the treading member, when the driving part rotates toward a front direction of the treading member.

3. The robotic prosthetic leg of claim 1,
   wherein the guide conduit has a first outer diameter smaller than an inner diameter of the first elastic member, and
   wherein a fixing part is formed at a rear side of the guide conduit and the fixing part has a second outer diameter corresponding to the inner diameter of the first elastic member.

4. The robotic prosthetic leg of claim 1, further comprising:
   a support bracket disposed at a upper side of the driving part, and having an adjusting opening through which the rear end of the wire passes; and
   an adjusting part having a stopper and an adjuster, wherein the stopper is combined with the rear end of the wire which passes through the adjusting opening to be extended to an outside of the adjusting opening, wherein the adjuster is screwed together with the adjusting opening and is closely rotated with respect to the stopper to adjust a height of the stopper.

5. The robotic prosthetic leg of claim 1, further comprising:
a second elastic member disposed between the first ankle bracket and the driving part,
wherein the second elastic member provides an elastic force so as to maintain an angle between the driving part and the treading member to be a predetermined basic angle, when an external force is not applied.

6. The robotic prosthetic leg of claim 5, wherein the second elastic member is a torsion spring,
wherein the driving part has a first fixing hole at which a first end of the second elastic member is inserted and fixed, and
wherein the first ankle bracket has a second fixing hole at which a second end of the second elastic member is inserted and fixed.

7. The robotic prosthetic leg of claim 6, wherein the first ankle bracket further comprises:
a fixing protrusion with which the second elastic member is rolled up; and
an incision hole through which the first end of the second elastic member passes, so that the first end of the second elastic member extends to outside.

8. A method for driving the robotic prosthetic leg of claim 1, the method comprising:
a treading step in which the treading member treads a ground and the driving part rotates toward a front direction of the treading member, so that the wire is pulled backwardly and the first elastic member is compressed by the pressing part;
a rolling step in which the driving part rotates toward a rear direction of the treading member, so that the treading member kicks the ground; and
a toe-offing step in which the treading member is off the ground.

9. The method of claim 8, wherein in the rolling step,
the first elastic member is elongated to provide an additional rotating force so that the driving part rotates toward the rear direction of the treading member.

10. The method of claim 8, wherein a second elastic member is disposed between the first ankle bracket and the driving part,
wherein a first end of the second elastic member is fixed to the driving part and a second end of the second elastic member is fixed to the first ankle bracket, and
wherein the second elastic member provides an elastic force so as to maintain an angle between the driving part and the treading member to be a predetermined basic angle, in the toe-offing step.

* * * * *